United States Patent [19]

Peters

[11] Patent Number: 5,788,640

[45] Date of Patent: Aug. 4, 1998

[54] SYSTEM AND METHOD FOR PERFORMING FUZZY CLUSTER CLASSIFICATION OF STRESS TESTS

[76] Inventor: Robert Mitchell Peters, 151 Marshall Ave., Floral Park, N.Y. 11001

[21] Appl. No.: 548,734

[22] Filed: Oct. 26, 1995

[51] Int. Cl.[6] .................................................. A61B 5/02
[52] U.S. Cl. ........................... 600/483; 600/481; 128/920; 395/924
[58] Field of Search ....................... 128/630, 668, 128/670, 700, 920, 923, 924; 364/413.01, 413.02; 395/22, 51, 61, 900, 924; 600/300, 481, 483, 513

[56] References Cited

U.S. PATENT DOCUMENTS

| | | |
|---|---|---|
| 4,525,775 | 6/1985 | Eydelman . |
| 4,694,418 | 9/1987 | Ueno et al. . |
| 4,855,910 | 8/1989 | Bohning . |
| 5,005,143 | 4/1991 | Altschuler et al. . |
| 5,156,158 | 10/1992 | Shirasaki . |
| 5,179,643 | 1/1993 | Homma et al. . |
| 5,263,120 | 11/1993 | Bickel . |
| 5,271,411 | 12/1993 | Ripley et al. . |
| 5,311,867 | 5/1994 | Kynor . |
| 5,312,443 | 5/1994 | Adams et al. . |
| 5,341,323 | 8/1994 | Yamakawa . |
| 5,422,984 | 6/1995 | Iokibe et al. ............................ 395/51 |
| 5,584,297 | 12/1996 | Bodoet et al. ........................ 128/668 |

OTHER PUBLICATIONS

R.M. Peters et al., "Fuzzy Cluster Analysis of Positive Stress Tests, a New Method of Combining Exercise Test Variables to Predict Extent of Coronary Artery Disease", American Journal of Cardiology, vol. 76, Oct. 1, 1995, pp. 648–651.

Primary Examiner—Jennifer Bahr
Assistant Examiner—Bryan K. Yarnell
Attorney, Agent, or Firm—Dilworth & Barrese

[57] ABSTRACT

A stress test classifying system and method classify current stress test data using a processor for comparing the current stress test with previous stress test data grouped in fuzzy sets and for generating a classification of the current stress test data with respect to the fuzzy sets.

20 Claims, 6 Drawing Sheets

| Degree of Membership | 0.0 | 0.1 | 0.2 | 0.3 | 0.4 | 0.5 | 0.6 | 0.7 | 0.8 | 0.9 | 1.0 | |
|---|---|---|---|---|---|---|---|---|---|---|---|---|
| Variable | | | | | | | | | | | | |
| $S_1$ | | 1/2 mm | 1 mm up | 1 mm flat | 1 mm down | 1 1/2 mm | 2 mm flat | 2 mm down or 2 1/2 mm | ST elev. | 3 mm | >3 mm | |
| $S_2$ | 40 | 40-35 | 35-30 | 30-25 | 25-20 | 20-15 | 15-10 | 10-5 | 5-(5) | (5-15) | >(15) | (mm Hg) |
| $S_3$ | 12 | 12-11 | 11-10 | 10-9 | 9-8 | 8-7 | 7-6 | 6-4.5 | 4.5-3 | 3-1 | <1 | (minutes) |
| $S_4$ | 100 | 100-95 | 95-90 | 90-85 | 85-80 | 80-75 | 75-70 | 70-65 | 65-60 | 60-50 | <50 | (%) |
| $S_5$ | 13 | 13-12 | 12-11 | 11-9 | 9-7.5 | 7.5-6 | 6-4.5 | 4.5-3 | 3-2 | 2-1 | 1-0 | (minutes) |
| $S_6$ | | 0-1 | 1-2 | 2-3 | 3-4 | 4-5 | 5-6 | 6-7 | 7-9 | 9-11 | >11 | (minutes) |

Fig. 2

| | Number of Coronary Arteries Narrowed > 50% | | | | |
|---|---|---|---|---|---|
| | Normal (9) | 1 (28) | 2 (30) | 3 (27) | 4* (15) |
| Mild 0.5 - 1.5 mm | 8/9 (88%) 9/9 (100%) | 16/28 (57%) 18/28 (64%) | 7/30 (23%) 14/30 (46%) | 0 0 6/27 (22%) | 0 0 2/15 (13%) |
| Moderate 2 - 2.5 mm | 1-9 (12%) 0 | 11/28 (39%) 9/28 (32%) | 12-30 (40%) 8/30 (27%) | 7/27 (26%) 9/27 (33%) | 3/15 (20%) 5/15 (33%) |
| Severe ≥3 mm** | 0 0 | 1/28 (4%) 1/28 (4%) | 11/30 (37%) 8/30 (27%) | 20/27 (74%) 12/27 (45%) | 12/15 (80%) 8/15 (54%) |

Fig. 5

SYSTEM AND METHOD FOR PERFORMING FUZZY CLUSTER CLASSIFICATION OF STRESS TESTS

BACKGROUND OF THE INVENTION

1. Field of the Invention

This disclosure relates to medical diagnostic systems, and in particular to a system and method for using fuzzy clustering techniques to classify stress tests.

2. Description of the Related Art

Previous medical studies of stress have used sharp cut-off points between normal and abnormal conditions, such as the depressions in the ST segment of the QRST waveform of heartbeat signals. From such studies, guidelines for the interpretation of positive stress tests have been formulated, but the application of such guidelines has provided only general assistance to clinicians in the interpretation of positive stress tests. In addition, some studies have used Bayesian or discriminant function analysis to demonstrate the importance of using different stress test variables to predict the extent of coronary artery disease (CAD). However, the results of these studies generally do not enable clinicians to simultaneously combine several stress test variables, each having a range of abnormality, to provide an accurate interpretation of positive stress tests.

Based mainly on Bayesian probability methods, known attempts to combine ST segment changes with other exercise variables have produced varied results. Although Bayesian inference may be appropriate for tests where there is a sharp cut-off between positive and negative test evaluations, it may not provide sufficient diagnostic accuracy for certain real world situations where there is a gradation of conditions of abnormality from "mildly" abnormal to "severely" abnormal. In addition, such cut-offs may neglect the contribution of information from variables in the mildly abnormal or normal range. Generally, each of the commonly used stress test variables, the degree of underlying CAD, and the interpretation of the stress test itself use continuing ranging in values from "very mild" to "very severe", so sharp cut-off points may have multiple degrees of abnormality grouped together resulting in reduced diagnostic accuracy.

Fuzzy techniques, including fuzzy set theory, fuzzy logic, and fuzzy clustering, have been developed as alternative methods for handling data having a graded degree of abnormality. Such fuzzy techniques retain a strong linguistic connection with commonly used descriptive terms such as "moderately abnormal" or "very severe".

For example, as described in U.S. Pat. No. 5,156,158, "normal" blood pressure may be associated with a range of values in a first set, and abnormal blood pressure, such as "high" blood pressure and "low" blood pressure, may be associated with ranges of values in a second and third set, respectively. Since such terms as "normal", "high", and "low" are typically associated with blood pressure and are relative terms, the ranges of values may overlap; i.e. the first set may have values common to each of the second and third sets.

Other applications have applied clustering methods, including fuzzy clustering methods, for extracting patterns from data with respect to multiple features and feature spaces.

Heretofore, the application of fuzzy set theory and clustering techniques have not been implemented to provide accurate classification of positive stress tests, including combinations of several stress tests. In addition, the feasibility of applying fuzzy cluster analysis to generate accurate classifications has not been demonstrated.

SUMMARY

A stress test classifying system and method are disclosed for classifying current stress test data using a processor for comparing the current stress test with previous stress test data grouped in fuzzy sets and for generating a classification of the current stress test data with respect to the fuzzy sets.

BRIEF DESCRIPTION OF THE DRAWINGS

The features of the disclosed stress test system and method will become more readily apparent and may be better understood by referring to the following detailed description of an illustrative embodiment of the present invention, taken in conjunction with the accompanying drawings, where:

FIG. 2 illustrates a table of ranges of values of fuzzy sets;

FIG. 5 illustrates an analysis of previous stress test data in a stress test database;

DESCRIPTION OF THE PREFERRED EMBODIMENTS

Figure 1:
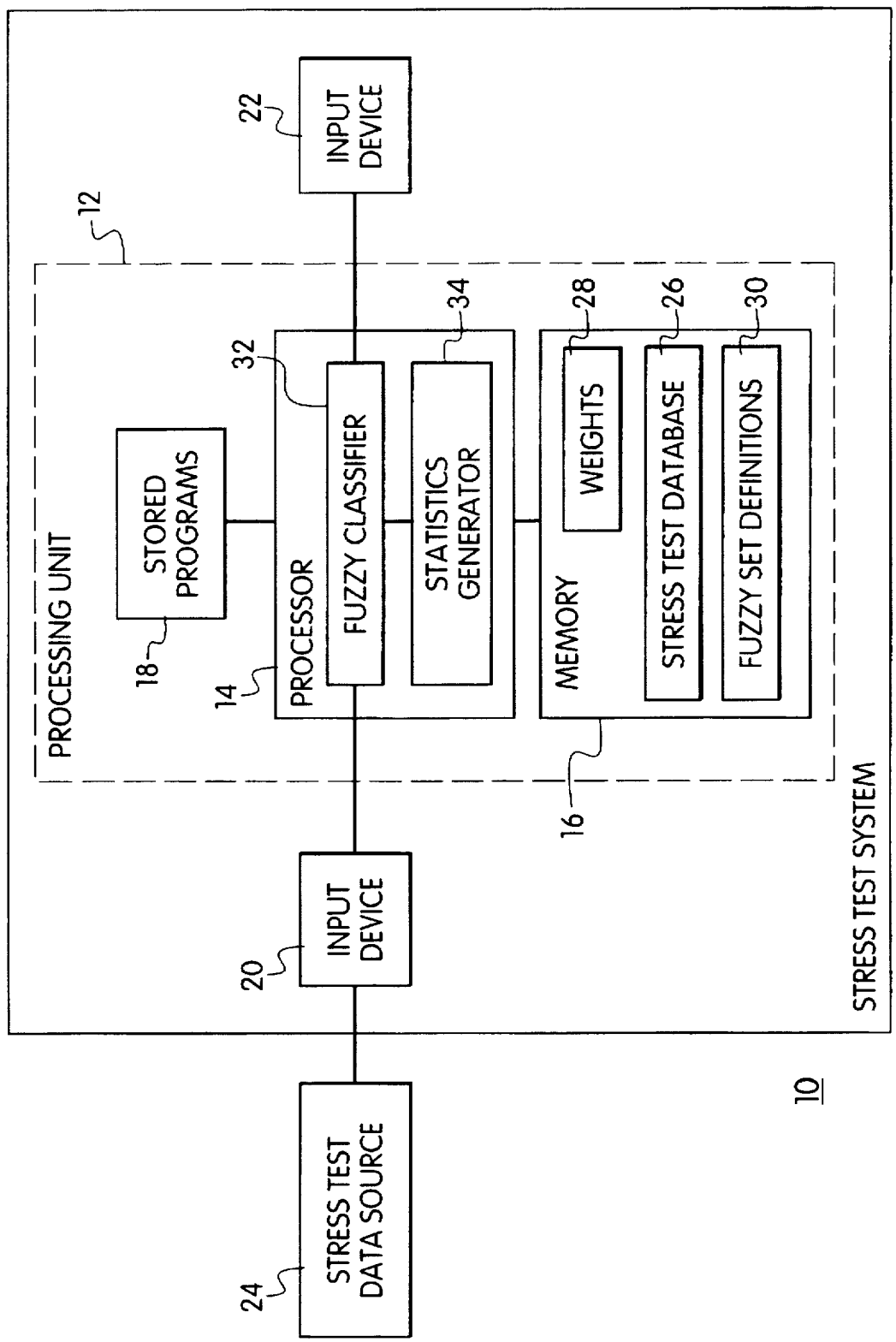
FIG. 1 illustrates the disclosed system for fuzzy clustering classification of stress tests.

Referring now in specific detail to the drawings, with like reference numerals identifying similar or identical elements, as shown in FIG. 1, the present disclosure describes a stress test system 10 and method for fuzzy clustering classification of stress tests. The stress test system 10 includes a processing unit 12 having a processor 14, memory 16, and stored programs 18, with the processing unit 12 operatively connected to an input device 20 and an output device 22.

For clarity of explanation, the illustrative embodiments of the disclosed stress test system 10 and method are presented as having individual functional blocks, which may include functional blocks labelled as "processor" and "processing unit". The functions represented by these blocks may be provided through the use of either shared or dedicated hardware, including, but not limited to, hardware capable of executing software. For example, the functions of processors and processing units presented herein may be provided by a shared processor or by a plurality of individual processors. Moreover, the use of the functional blocks with accompanying labels herein is not to be construed to refer exclusively to hardware capable of executing software. Illustrative embodiments may include digital signal processor (DSP) hardware, such as the AT&T DSP16 or DSP32C, read-only memory (ROM) for storing software performing the operations discussed below, and random access memory (RAM) for storing DSP results. Very large scale integration (VLSI) hardware embodiments, as well as custom VLSI circuitry in combination with a general purpose DSP circuit, may also be provided. Any and all of these embodiments may be deemed to fall within the meaning of the labels for the functional blocks as used herein.

In an exemplary embodiment, the disclose stress test system 10 may be implemented using a personal computer employing, for example, a PENTIUM™ microprocessor, available from INTEL™ CORPORATION as the processor 14, with about 8 MB of RAM and a hard or fixed drive having about 1 GB storage capacity as the memory 16. The memory 16 may store the stored programs 18, which may be compiled or interpreted source code written, for example, in C++ for performing the functions of the disclosed stress test system 10 and method, as described in greater detail below.

The input device 20 allows inputs from a user to the stress test system 10; for example, a keyboard may be used for inputting commands and stress test data, such as current stress test data corresponding to a current or specific patient, and previous stress test data which is used to classify the current stress test data. The input device 20 may also include a floppy disk drive or other data reading devices for accessing transferable storage media, such as floppy disks, magnetic tapes, compact disks, or other storage media for providing the previous stress test data.

It is also understood that other input devices 20 may also be used to receive commands from the user, such as user-actuated buttons employed and associated with specific functions for user input, mouse devices, and graphical user interfaces (GUI) such as WINDOWS™ available from MICROSOFT™ CORPORATION. Other alternative input devices 20 may include microphones for receiving audio voice commands, with the processing unit 12 including speech or voice recognition devices and/or software known in the art to accept commands and to operate the processing unit 12.

The output device 22 may include a display and/or a printer for outputting, for example, a classification of a current stress test as indicating a mild, moderate, or severe condition of stress. Other outputs may include a graphical representation of the current stress test of the current patient with respect to the previous stress test data.

The previous stress test data may be received through the input device 20 from a stress test data source 24, such as a patient database associated with a hospital mainframe computer. The received stress test data may then be stored in a stress test database 26 in the memory 16, and may be accessed by the stored programs 18 to classify the current stress test data. The memory 16 also stores weights 28 and fuzzy set definitions 30, which may include corresponding labels such as "mild", "moderate", and "severe", as described below.

The processor 14 may include a fuzzy classifier 32 for classifying the current stress test data using the weights 28 and the fuzzy set definitions 30 which determine the fuzzy membership functions. The processor 14 may optionally include a statistics generator 32 for determining statistics of data groups defined by a user in order to assist the user in refining the fuzzy set membership functions used by the fuzzy classifier 32. The fuzzy classifier 32 and statistics generator 34 may be implemented in hardware or firmware using integrated circuits (ICs) or chips, or the fuzzy classifier 32 and statistics generator 34 may be implemented in software by the stored programs 18 executed by the processor 14.

The disclosed stress test system 10 uses fuzzy cluster analysis to combine, for example, six exercise test variables to classify a patient's condition, reflected in the patient's current stress test data, as either mildly, moderately, or severely abnormal with respect to the previous stress test results stored in the stress test database 26. Stress tests classified using such multiple variable analysis generally have a better correlation with the extent of CAD than, for example, the degree of ST depression alone, and may be especially helpful in predicting both mild and high grade CAD. It is understood that the disclosed stress test system 10 and method may be implemented using a plurality of test variables and so they are not limited to the six test variables described below.

The six variables used by the disclosed stress test system 10 are: the ST segment change; the difference between resting systolic and peak exercise systolic blood pressure; total treadmill time; peak exercise heart rate as a percentage of 100% predicted maximum for age; time to onset of angina; and duration of repolarization abnormalities.

Upon inputting the current stress test data as the values of the six variables of the current patient, the disclosed stress test system 10 and method receive and process these values to generate a similarity measure to determine how closely each stress test resembles a prototypical mildly, moderately, or severely abnormal stress test. Unlike stress tests making a diagnosis based sole on mild degrees of ST depression (0.5 to 1.5 mm), tests classified as mild by the disclosed stress test system 10 and method generally exclude high grade CAD. Tests classified as severe are associated with severe CAD, are better in detecting, for example, left main and triple vessel CAD than tests with 3 mm or more of ST depression, and are useful in detecting high grade CAD in patients exhibiting mild degrees of ST depression when other stress test variables may indicate such high grade CAD. Combining stress test variables by fuzzy cluster analysis is thus generally useful in the evaluation and management of patients with positive exercise tests.

In an exemplary embodiment, the stress test database 26 may include positive stress tests from 109 patients, with the data of these stress tests being provided from a stress test data source 24, such as floppy disks storing the stress test data of the 109 patients. The 109 patients are selected out of 1357 Bruce protocol exercise treadmill tests. The stress test data for each of the 109 patients was selected for entry in the stress test database 26 using predetermined criteria; for example, if the stress test data had 0.5 mm or more of exercised-induced ST segment depression or $\geq 1$ mm of exercised-induced ST segment elevation, and if the respective patents had undergone cardiac angiography within four weeks before or after the stress test. Stress test results were excluded if the respective patients had a coronary angioplasty or coronary bypass surgery at any time prior to the stress test, if they had known valvular, hypertensive, or congenital heart disease, if they had a left bundle branch block, if they had significant chronic lung disease or peripheral vascular disease, or if they were taking beta-blockers or Digoxin at the time of the exercise test. Stress test results were not excluded for resting ST segment depression. Q waves, T wave inversions, or right bundle branch block on resting EKG.

The stress test data of the 109 patients meeting the above criteria are thus provided to the stress test database 26, where angiograms performed within one month of the stress tests showed that 100 of these patients had been diagnosed with CAD (15 left main, 27 triple vessel, 30 double vessel, 28 single vessel disease) and 9 were considered normal. Of the 109 patients, 90 were males and 19 were females ranging in age from 37 to 78. Of these 109 patients, 61% had typical angina, 22% had atypical symptoms, 17% were asymptomatic, and 17% had a previous myocardial infarction. On the day of the stress test, 16% had taken nitrates, 8% had taken calcium blockers, and 3% had taken aspirin.

Angiograms on these patients showed 15 to have left main CAD, 27 had triple vessel CAD, 30 had double vessel CAD, 28 had single vessel CAD, and 9 were normal. For purposes of 3 vessel classification, a lesion was considered significant if considered to be greater than 50% by the visual estimation of the angiographer. Each patient was also assigned a coronary score according to the method of Friesinger; for example, as described in A. Moise et al., "Clinical and Angiographic Correlates and Prognostic Significance of the Coronary Extent Score", AMERICAN JOURNAL OF CARDIOLOGY, 1988, pp. 61:1255–1259. Of the 109 stress tests, 49 had ST depression of 0.5 to 1.5 mm, 31 had ST depression of 2 to 2.5 mm, and 29 had ST depression of 3 mm or more, or had ST elevation. Only one patient with CAD had 0.5 mm ST depression on exercise, and only one patient had ST elevation.

It is understood that the disclosed stress test system 10 and method may operate using a stress test database 26 including previous stress test data from other patients and selected using other criteria. Accordingly, it is to be understood that the disclosed stress test system 10 and method determines the condition of a current patient with respect to the particular stress test database 26 employed, and the accuracy of classification may be determined using, for example, statistical analysis, such as described below and using the optional statistics generator 34.

As described above the six stress test variables are labelled as follows: ST segment change in mm ($S_1$), difference between resting systolic and peak exercise systolic blood pressure ($S_2$), total exercise treadmill time ($S_3$), peak exercise heart rate expressed as a percentage of 100% predicted maximum heart rate for age ($S_4$), time to onset of angina, defined as chest pain or typical anginal symptom but not including dyspnea or fatigue during exercise ($S_5$), and duration of repolarization abnormalities (ST segment changes and/or T wave changes) after termination of exercise ($S_6$). It is to be understood that the labels $S_1$–$S_6$ is arbitrary, and the stress test variables may be labelled in any order.

The disclosed stress test system 10 and method constructs fuzzy sets for each of the above stress test variables, with the degree of membership corresponding to the severity of the abnormality for each variable listed in FIG. 2 to specify the fuzzy set definitions 30.

Let $u_x(S_i)\epsilon[0,1]$ denote the membership grade in the fuzzy set characterizing the stress test of the patient X under test, and defined on the set $S=\{S_1,S_2,S_3,S_4,S_5,S_6\}$ which indicates the severity of abnormality for the variable $S_i$ in the patient's stress test. To classify a patient's stress test as mildly ($d_1$), moderately ($d_2$) or severely ($d_3$) abnormal, a clustering technique may be used to determine the prototypical stress test ($d_1,d_2,d_3$) which is most similar to the patient's stress test. The prototypes of mildly, moderately, and severely abnormal stress tests may be based on accepted values for the range of each variable and may be described by the matrices:

|   | | $S_1$ | $S_2$ | $S_3$ | $S_4$ | $S_5$ | $S_6$ | |
|---|---|---|---|---|---|---|---|---|
| $d_1 =$ lower | \| | .1 | 0 | 0 | 0 | 0 | .1 | \| |
|  upper | \| | .3 | .2 | .3 | .3 | .3 | .4 | \| |

|   | | $S_1$ | $S_2$ | $S_3$ | $S_4$ | $S_5$ | $S_6$ | |
|---|---|---|---|---|---|---|---|---|
| $d_2 =$ lower | \| | .4 | .3 | .4 | .4 | .4 | .5 | \| |
|  upper | \| | .6 | .6 | .6 | .6 | .6 | .7 | \| |

|   | | $S_1$ | $S_2$ | $S_3$ | $S_4$ | $S_5$ | $S_6$ | |
|---|---|---|---|---|---|---|---|---|
| $d_3 =$ lower | \| | .7 | .7 | .7 | .7 | .7 | .8 | \| |
|  upper | \| | 1 | 1 | 1 | 1 | 1 | 1 | \| |

A fuzzy relation W is then defined on the set of variables and prototypes; i.e. fuzzy sets, that assigns weights 28, which are stored in memory 16, to specify the importance or pertinence of each variable $S_i$ in these prototypes. The relation W of these weights of relevance may be based on known values, and may be, for example, given by:

$$W = \begin{array}{c} \\ S_1 \\ S_2 \\ S_3 \\ S_4 \\ S_5 \\ S_6 \end{array} \begin{array}{ccc} d_1 & d_2 & d_3 \\ \left[\begin{array}{ccc} .8 & .9 & .7 \\ .5 & .5 & .2 \\ .5 & .6 & .4 \\ .4 & .5 & .4 \\ .6 & .7 & .4 \\ .5 & .6 & .4 \end{array}\right] \end{array}$$

Let $u_w(S_i,d_j)$ denote the weight of each variable for each prototype $d_j$. To determine which prototype (mild=$d_1$, moderate=$d_2$, severe=$d_3$) is most similar to the current patient's stress test, a similarity measure $D_P$ between the patient's stress test variables and those typical of each prototype ($d_j$) is computed. In the exemplary embodiment, this similarity measure $D_P$ is based on the Minkowski distance using a modified Euclidean metric with, for example, p=2, and is given by:

$$D_p(d_j,x) = \left[ \sum_{i\epsilon A_j} u_w(S_i,d_j)(u_{dj1}(S_i) - u_x(S_i))^p + \sum_{i\epsilon B_j} u_w(S_i,d_j)(u_{dju}(S_i) - u_x(S_i))^p \right]^{\frac{1}{p}}$$

where $A_j=\{i|u_x(S_i)<u_{dj1}(S_i), 1\leq i \leq m\}$
$B_j=\{i|u_x(S_i)>u_{dju}(S_i), 1\leq i \leq m\}$ and m equals the total number of variables. For the disclosed stress test system 10 and method, m=6; i.e. for the six stress test variables $S_1$–$S_6$ used by the disclosed stress test system 10 and method. It is to be understood that other similarity measures may be defined to classify the current stress test data as corresponding to one specific prototype or fuzzy set more that to the others.

For all possible prototypes, the similarity measure that has a minimum value corresponds to the prototype stress test that most closely resembles the patient's stress test. A similar fuzzy cluster method was used by Esogbue and Elder in examining the similarity between a patient's symptoms and the prototypical symptom patterns seen in various diseases, as described in, for example, A. Esogbue et al., "Measurement and Validation of a Fuzzy Mathematical Model for Medical Diagnosis", FUZZY SETS AND SYSTEMS, 1983, pp. 10:223–242.

The minimum similarity measure thus determines a crisp output value from the prototypes to defuzzify the current stress test data with respect to the prototypes. One skilled in the art may use other defuzzification techniques, such as the center-of-gravity methods known in the art, for generating crisp output values to classify the input current stress test data.

In one example, a current patient may undergo an exercise stress test with the following results:

ST segment: 1.5 mm horizontal depression, which corresponds to $S_1=0.5$, according to the table in FIG. 2;

systolic blood pressure change: decreased 20 mm, so $S_2=1$;

total exercise time: 5 minutes, so $S_3=0.7$;

peak heart rate: 85% predicted maximum for age, so $S_4=0.4$;

time to angina: 2 minutes, 50 seconds, so $S_5=0.8$; and duration of repolarization abnormalities: 9 minutes, so $S_6=0.9$.

Therefore, $$D_2(d_1,x)=[(0.8)(0.3-0.5)|^2+(0.5)(0.2-1)|^2+(0.5)(0.3-0.7)|^2+(0.4)(0.3-0.4)|^2+(0.6)(0.3-0.8)|2+(0.5)(0.4-0.9)|^2]^{1/2}=0.616.$$

$$D_2(d_2,x)=[(0.5)(0.6-1)|^2+(0.6)(0.6-0.7)|^2+(0.7)(0.6-0.8)|^2+(0.6)(0.7-0.9)|^2]^{1/2}=0.279.$$

$$D_2(d_3,x)=[(0.7)(0.7-0.5)|^2+(0.4)(0.7-0.4)|^2]^{1/2}=0.184.$$

Therefore, the stress test of the patient in the example above is most similar to the prototype $d_3$ (severe abnormality), as this similarity measure yields the minimum value. Accordingly, the stress test system 10 and method classifies the current stress test data of the current patient as being a severely abnormal stress test.

The disclosed stress test system 10 and method may also allow the user to customize the fuzzy sets; i.e. the prototypes, by modifying the ranges of data of FIG. 2 corresponding to the membership functions defining groups as the fuzzy sets. Using the statistics generator 30, the user may analyze the data between the groups of the previous stress test data in the stress test database 26 by comparing the variance of the groups included in the fuzzy sets and by using an unpaired "t" test. Data within a single group may be compared by a paired "t" test, and correlations of the data are determined by calculation of the Pearson coefficient of correlation. A chi-square analysis may also be used to assess for potential differences in proportions among groups. The "t" tests may be 2 tailed, with an associated p value of less than 0.05 being considered statistically significant.

Figure 4:
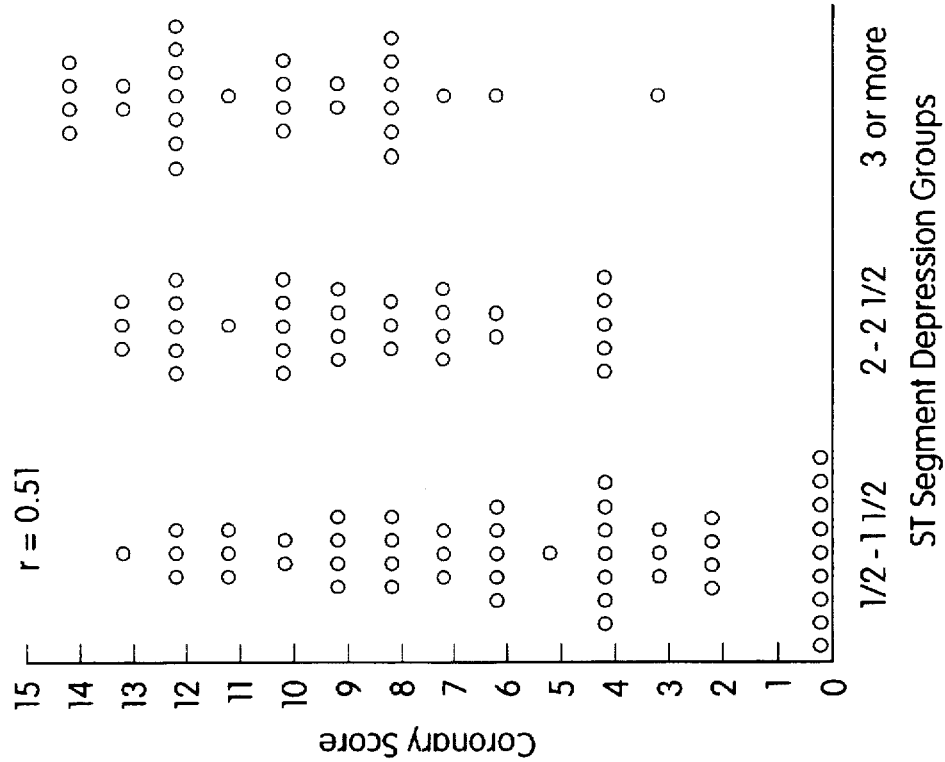
FIG. 4 illustrates a graph of the stress test data of FIG. 3 grouped and plotted with respect to ST segment depression groups.
Figure 3:
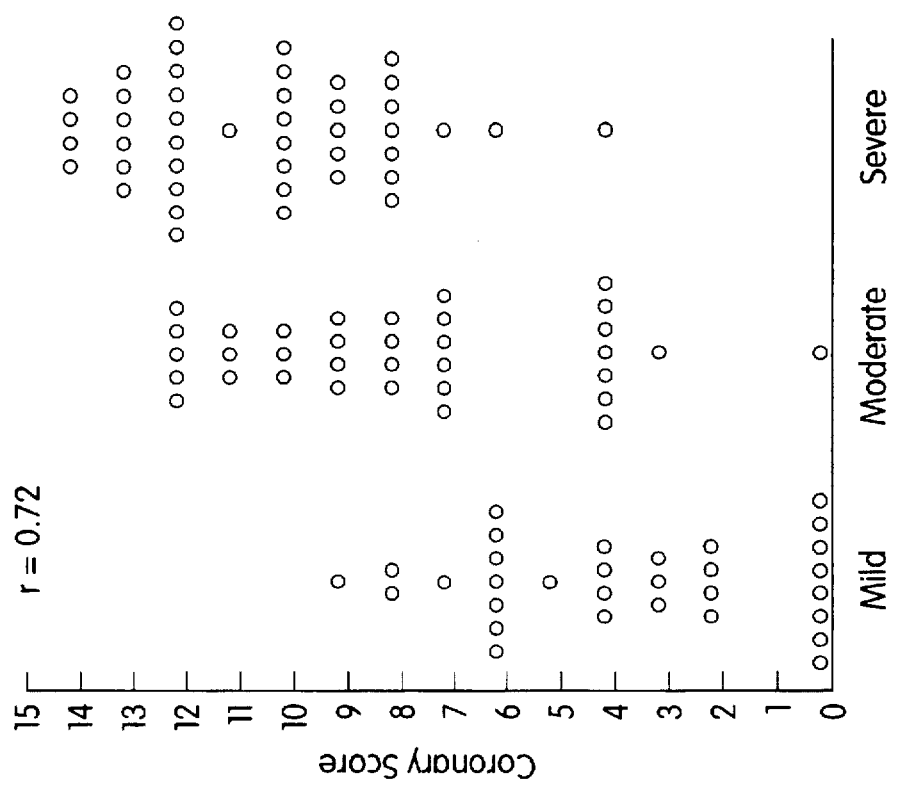
FIG. 3 illustrates a graph of stress test data grouped and plotted in fuzzy clusters.

For example, for the previous stress test data in the database 26, with the prototypes for "mild", "moderate", and "severe" conditions defined above, a significant difference is found between the average coronary scores for the tests classified as "mild" (3.61), "moderate" (7.76), and "severe" (10.52) by the fuzzy cluster method (p<0.05). As shown in FIG. 3, the fuzzy cluster method has an overall better correlation with a coronary score r=0.72 than did graded ST depression alone, with r=0.51, shown in FIG. 4.

A test classified as "mild" by the disclosed stress test method excluded high grade CAD. No patient having stress test data classified as "mild" had a coronary score above 9, only 12.9% of the patients had a coronary score above 6, and no patients had triple vessel or left main disease. This is in contrast to the 0.5 to 1.5 mm ST depression group where 18.4% of the patients had a coronary score above 9, 12.2% had triple vessel disease, and 4.2% had left main CAD. Even for patients with double vessel CAD, patients classified as "mild" had lower average coronary score of 7.14 compared to an average coronary score of 8.00 for the 0.5 to 1.5 mm ST depression group (p<0.05).

Tests classified as "severe" by the disclosed stress test method were associated with high grade CAD. For "severe" tests, 77.3% of the patients had a coronary score of 9 or more, while for tests in the 3 mm or more ST depression group, 68.9% had a coronary score of 9 or greater. For patients with triple vessel disease, 74% had stress tests classified as "severe", while only 45% of stress tests in patients with triple vessel CAD had 3 mm or more ST depression, as shown in FIG. 5. For patients with left main CAD, the disclosed stress test method classified 80% of their tests as severe, while only 54% of left main patients had tests showing 3 mm or more ST depression. The 0.5 to 1.5 mm ST depression group is of interest, since the two patients with left main CAD are classified as "severe" by the disclosed stress test method. Thus whatever the degree of ST depression, tests classified as "severe" by the disclosed stress test method are strongly associated with high grade CAD.

Patients classified as "moderate" by the disclosed stress test method had a wide range of CAD (from single vessel to left main CAD) and a similar wide range of coronary scores (from 3 to 12, excluding the one normal patient in this group). Thus, as in the case of the 2 to 2.5 mm ST depression group in the stress test database 26, stress tests classified as "moderate" are not helpful in predicting the extent of CAD.

Using the disclosed stress test system 10 and method, several stress test variables are combined using fuzzy cluster analysis to provide both a feasible and a relatively accurate classification of positive stress tests. The resulting classification of positive stress tests as either "mildly", "moderately", or "severely" abnormal indicates a relationship to the severity of the underlying CAD. The disclosed stress test system 10 and method generally predicts both mild and high grade CAD better than ST segment depression alone.

Figure 6:
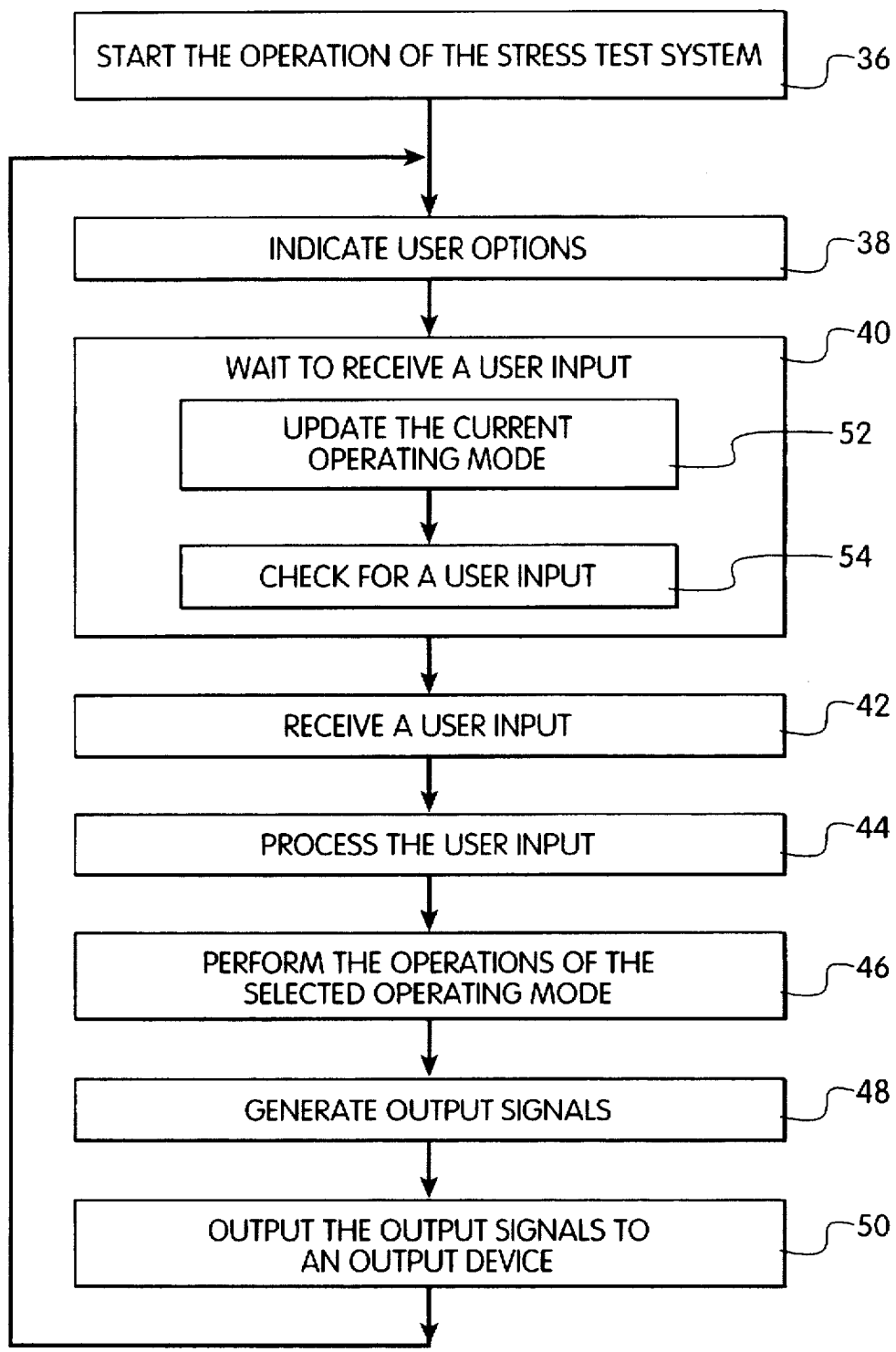
FIG. 6 illustrates a method of operation of the disclosed stress test system.
Figure 7:
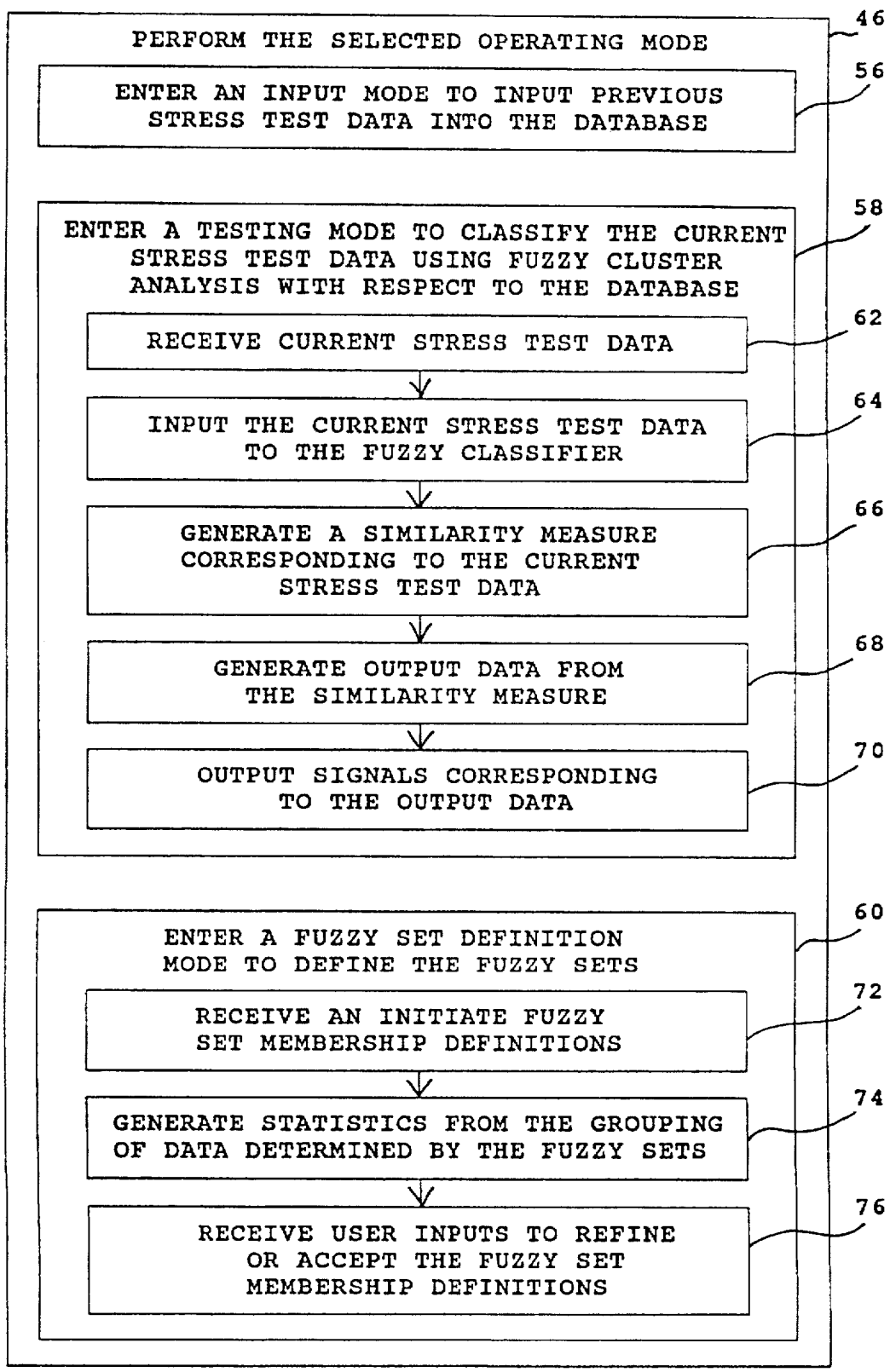
FIG. 7 illustrates a method for performing selected modes of operation of the disclosed stress test system.

In use, the disclosed stress test system 10 and method performs the steps in FIGS. 6–7. As shown in FIG. 6, the main operating program performs the steps of starting the operation of the stress test system in step 36; indicating user options to the user in step 38; waiting to receive a user input in step 40; receiving a user input in step 42; processing the user input in step 44; performing the operations of the selected operating mode in step 46; generating output signals in step 48; outputting the output signals to the output device 22 in step 50; and then looping back to wait for additional user inputs in step 30. The step of waiting to receive a user input in step 40 may include the steps of updating the current operating mode in step 52, and checking for a user input in step 54.

As shown in FIG. 7, the step 46 of FIG. 6 performs the selected operating mode which includes performing steps 56, 58, 60 to enter an input mode, a testing mode, and an optional fuzzy set definition mode, respectively, selected by the user. In step 56, the disclosed system 10 and method enters an input mode for inputting previous stress test data into the stress test database 26, as well as the weights 28 associated with the fuzzy relation W associated with the previous stress test data. This may include the steps of retrieving such stress test data from files on a storage medium and receiving such weights from a keyboard or an input file through the input device 20 in a manner known in the art.

In step 58, the stress test system 10 and method may enter a testing mode to classify the current stress test data using fuzzy cluster analysis with respect to the stress test database 26 by receiving current stress test data of a current patient in step 62; input the current stress test data to the fuzzy classifier 28 in step 64; and generating at least one similarity measure corresponding to the current stress test data in step 66; for example, the similarity measure may be generated for each fuzzy set or prototype, as described above.

Using the similarity measure, the stress test system 10 and method then generates output data from the similarity measure in step 68; for example, the output data may be a label or value, which may be stored in the memory 16, indicating the fuzzy set having the minimum similarity measure to thus classify the current patient's test data. The label may be data corresponding to the terms "mild", "moderate", and "severe".

The stress test system 10 and method then outputs signals in step 70 corresponding to the output data generated in step 72; for example, the output signals may be signals for controlling the output device 22 such as a display to output the labels "mild", "moderate", and "severe" indicating the classification of the patient's current stress test data with respect to the stress test database 26.

In step 58, the stress test system 10 and method may enter a fuzzy set definition mode to define the fuzzy sets, which may include the steps of receiving initial fuzzy set membership definitions, for example, from the user in step 72; generating statistics from the grouping of data determined by the fuzzy sets in step 74; and receiving user inputs to refine or accept the fuzzy set membership definitions in step 76, which may include displaying the groupings of data and the statistics, graphically illustrating the fuzzy sets, and updating the displayed statistics and graphics in response to changes in the fuzzy set definitions by the user.

One of the primary advantages of the disclosed stress test system 10 and method is the incorporation of a graded degree of abnormality for each of the stress test variables. Thus each variable, even if in normal range, provides some useful information in the determination of the abnormality of each stress test. Since there is no known standardized method of combining stress test variables, the disclosed stress test system 10 and method reflects the reasoning process that physicians perform in evaluating each variable when interpreting a positive stress test. In addition, the customization of the disclosed stress test system 10 and method may permit physicians to improve their evaluations.

Thus, the discloses stress test system 10 and method may facilitate the making of clinical decisions. Patients classified by the disclosed stress test system 10 and method as having mildly abnormal stress tests are correlated as having milder degrees of CAD for which continued medical therapy may be appropriate. Patients with severely abnormal stress test also have a high correlation with high grade CAD, and so may be strongly considered for angiography. For those with moderately abnormal tests, the clinician may choose stress echocardiography or nuclear stress testing to sort out which patients in this group may have higher degrees of CAD.

In addition, once the disclosed stress test system 10 and method is initiated and optionally customized, the classification of stress tests as "mildly", "moderately", or "severely" abnormal may be done quickly using the computational speed of the stress test system 10.

While the disclosed stress test system and method have been particularly shown and described with reference to the preferred embodiments, it is understood by those skilled in the art that various modifications in form and detail may be made therein without departing from the scope and spirit of the invention. The use of relatively large databases of patients for the stress test database 26 may provide improved accuracy of the classification, and the use of additional exercise variables or variables from nuclear stress tests or stress echocardiography may be performed to refine the disclosed stress test system 10 and method and to improve its ability to predict the extent of CAD. In addition, the disclosed system 10 and method may be implemented in a portable or compact embodiment to facilitate use by both large medical institutions and other medical practitioners. Accordingly, modifications such as those suggested above, but not limited thereto, are to be considered within the scope of the invention.

What is claimed is:

1. A stress test classifying system for classifying current stress test data comprising:

a processor for comparing the current stress test with previous stress test data grouped in fuzzy sets and for generating a classification of the current stress test data with respect to the fuzzy sets, the processor including:
a fuzzy classifier for generating a respective similarity measure for each fuzzy set using predetermined fuzzy set definitions and the current stress test data, and for generating a crisp value from the similarity measures to determine the classification.

2. The stress test classifying system of claim 1 further comprising:

a memory for storing the previous stress test data and the predetermined fuzzy set definitions.

3. The stress test classifying system of claim 1 further comprising:

a fuzzy classification program executable by the processor for implementing the fuzzy classifier.

4. The stress test classifying system of claim 3 wherein the fuzzy classifier includes:

means for generating the similarity measures from a predetermined metric applied to the current stress test data and the predetermined fuzzy set definitions.

5. The stress test classifying system of claim 3 wherein the fuzzy classifier includes:

means for generating a crisp value from a minimum value of the similarity measures.

6. The stress test classifying system of claim 4 wherein the means for generating the similarity measures applies a weighted Euclidean metric to the current stress test data, the predetermined fuzzy set definitions, and a plurality of weights associated with each fuzzy set definition.

7. The stress test classifying system of claim 1 wherein the processor generates the classification of the current stress test with respect to predetermined classes defined by fuzzy sets and with respect to a plurality of stress test variables.

8. The stress test classifying system of claim 7 wherein the plurality of stress test variables include six predetermined stress test variables.

9. The stress test classifying system of claim 1 wherein the processor includes:

a statistics generator for generating statistics of the previous stress test data grouped in the fuzzy sets to facilitate refinement of the fuzzy sets.

10. A stress test classifying system for classifying current stress test data comprising:

a memory for storing previous stress test data in a database, fuzzy set definitions grouping the previous stress test data in a plurality of fuzzy sets, and a plurality of weights associated with each fuzzy set and with a respective stress test variable;

a processor for comparing the current stress test with the previous stress test data, the processor including a fuzzy classifier for generating a crisp classification of the current stress test data with respect to the fuzzy sets using similarity measures for each respective fuzzy set with respect to each stress test variable using the predetermined fuzzy set definitions, the current stress test data, and the weights, wherein each similarity measure indicates a degree of similarity of the current stress test data to the respective fuzzy set.

11. The stress test classifying system of claim 10 wherein the fuzzy classifier includes:

means for generating the similarity measures from a multi-variable weighted Euclidean metric applied to the current stress test data and the predetermined fuzzy set definitions, wherein the multi-variable weighted Euclidean metric is weighted using the weights.

12. The stress test classifying system of claim 10 wherein the fuzzy classifier includes:

means for determining a minimum value of the similarity measures; and wherein the minimum value, as a crisp value, determines the classification of the current stress test with respect to the fuzzy sets and with respect to the plurality of stress test variables.

13. The stress test classifying system of claim 12 wherein the memory stores a plurality of labels, each associated with a respective fuzzy set; and wherein the processor, responsive to the minimum value, outputs a first label of the fuzzy set corresponding to the minimum value, wherein the first label indicates the classification of the current stress test data.

14. The stress test classifying system of claim 10 wherein the plurality of stress test variables include the group consisting of ST segment change, a difference between resting systolic and peak exercise systolic blood pressure, total treadmill time, peak exercise heart rate as a percentage of 100% predicted maximum for age, time to onset of angina, and duration of repolarization abnormalities.

15. The stress test classifying system of claim 10 wherein the processor includes:

a statistics generator for generating statistics of the previous stress test data grouped in the fuzzy sets to facilitate refinement of the fuzzy sets by the user using an input device.

16. A method for classifying current stress test data comprising the steps of:

(a) storing, in a memory, fuzzy set definitions grouping the previous stress test data in a plurality of fuzzy sets;

(b) storing, in the memory, a plurality of weights associated with each fuzzy set and with a respective stress test variable;

(c) operating a processor to generate a plurality of similarity measures for each respective fuzzy set with respect to each stress test variable using the predetermined fuzzy set definitions; and (d) operating a processor to generate a crisp value as the classification of the current stress test data with respect to the fuzzy sets using the plurality of similarity measures.

17. The method of claim 16 wherein the step (c) of operating the processor includes the steps of:

(c1) processing the current stress test data and the predetermined fuzzy set definitions to generate processed values;

(c2) weighting the processed values using a plurality of weights; and (c3) generating the similarity measures from a multi-variable Euclidean metric applied to the processed values.

18. The method of claim 16 wherein the step (c) of operating the processor includes the steps of:

(c1) determining a minimum value of the similarity measures; and wherein the step (d) of operating the processor including the steps of:

(d1) determining the classification of the current stress test with respect to the fuzzy sets and with respect to the plurality of stress test variables using the minimum value.

19. The method of claim 16 wherein step (d) further includes the steps of:

(d1) retrieving from the memory a first label associated with a first fuzzy set corresponding to the minimum value; and (d2) outputting the first label to indicate the classification of the current stress test data.

20. The method of claim 16 further including, before the step (c), the steps of:

(e) executing a fuzzy classification program using the processor to operate the processor to perform steps (c) and (d).

* * * * *